United States Patent [19]
Childers et al.

[11] Patent Number: 5,556,607
[45] Date of Patent: Sep. 17, 1996

[54] STERILIZATION APPARATUS AND METHOD FOR MULTICOMPONENT STERILANT

[75] Inventors: Robert W. Childers, Garner; James R. Rickloff, Cary; Thaddeus J. Mielnik, Apex, all of N.C.; Kenneth J. Klobusnik, Lake City, Pa.

[73] Assignee: American Sterilizer Company, Erie, Pa.

[21] Appl. No.: 530,577

[22] Filed: Sep. 19, 1995

Related U.S. Application Data

[62] Division of Ser. No. 279,688, Jul. 25, 1994, Pat. No. 5,492,672, which is a continuation of Ser. No. 851,415, Mar. 13, 1992, abandoned.

[51] Int. Cl.⁶ .................. A61L 2/20; A61L 9/00
[52] U.S. Cl. .............. 422/300; 422/292; 134/166 R; 134/170
[58] Field of Search ............... 422/26–28, 32–33, 422/292, 295, 300, 301, 905; 134/88–89, 170, 92, 166 R, 169 R; 433/104, 114, 132

[56] References Cited

U.S. PATENT DOCUMENTS

| | | | |
|---|---|---|---|
| Re. 33,007 | 8/1989 | Bier | 422/28 |
| 3,443,884 | 5/1969 | Linder | 422/296 |
| 3,773,466 | 11/1973 | Linder | 422/116 |
| 3,948,601 | 4/1976 | Fraser et al. | 422/23 |
| 4,064,886 | 12/1977 | Heckele | 134/171 |
| 4,117,597 | 10/1978 | Trist et al. | 433/132 |
| 4,164,538 | 8/1979 | Young et al. | 422/26 |
| 4,169,123 | 9/1979 | Moore et al. | 422/29 |
| 4,169,124 | 9/1979 | Forstrom et al. | 422/33 |
| 4,196,166 | 4/1980 | Sanderson et al. | 422/33 |
| 4,203,943 | 5/1980 | Gillis et al. | 422/27 |
| 4,230,663 | 10/1980 | Forstrom et al. | 422/33 |
| 4,239,731 | 12/1980 | Gillis et al. | 422/27 |
| 4,261,950 | 4/1981 | Bainbridge et al. | 422/26 |
| 4,278,101 | 7/1981 | Tanaka et al. | 134/171 |
| 4,281,674 | 8/1981 | Tanaka et al. | 134/171 |
| 4,282,179 | 8/1981 | Gunther | 422/27 |
| 4,294,804 | 10/1981 | Baran | 422/27 |
| 4,296,067 | 10/1981 | Nasman et al. | 422/26 |
| 4,299,244 | 11/1981 | Hirai | 134/170 |
| 4,335,071 | 6/1982 | Thornton | 422/26 |
| 4,337,223 | 6/1982 | Kaye | 422/112 |
| 4,348,357 | 9/1982 | Bithell | 422/22 |
| 4,372,916 | 2/1983 | Chamberlain et al. | 422/111 |
| 4,380,530 | 4/1983 | Kaye | 422/300 |
| 4,410,492 | 10/1983 | Kaye | 422/27 |
| 4,435,194 | 3/1984 | Picard et al. | 422/29 |
| 4,449,518 | 5/1984 | Konomura et al. | 128/4 |
| 4,489,741 | 12/1984 | Ogasawara | 134/179 |
| 4,525,220 | 6/1985 | Sasa et al. | 422/33 |
| 4,526,622 | 7/1985 | Takamura et al. | 422/33 |
| 4,526,623 | 7/1985 | Ishii et al. | 134/21 |
| 4,537,209 | 8/1985 | Sasa | 134/102 |
| 4,544,355 | 10/1985 | Eibofner et al. | 433/104 |

(List continued on next page.)

*Primary Examiner*—Robert Warden
*Assistant Examiner*—Hien Tran
*Attorney, Agent, or Firm*—Jones, Day, Reavis & Pogue

[57] ABSTRACT

The present invention provides a sterilization process particularly well suited for sterilizing instruments and other devices having long narrow lumens. Apparatus in which the process can be practiced is also provided. The process uses a multicomponent sterilant vapor wherein one component is water. The lumened instruments are fluidly connected to the exhaust manifold of the sterilizer. A deep vacuum is drawn in the sterilization chamber followed by the injection of pulses of the sterilant vapor until a higher, but still subatmospheric pressure level is reached. When the pressure level reaches a predetermined subatmospheric level, a flow-through sterilization phase begins. It includes successive alternating periods of sterilant flow and the discontinuance of such flow. During sterilant flow periods, there are sterilant injection pulses where the sterilant flows through the chamber and the lumened instruments to exhaust. Each such flow period is followed by a hold period. Following the sterilization phase, there are one or more aeration steps to remove sterilant from the chamber.

6 Claims, 6 Drawing Sheets

U.S. PATENT DOCUMENTS

| | | | |
|---|---|---|---|
| 4,579,597 | 4/1986 | Sasa et al. | 422/33 |
| 4,579,598 | 4/1986 | Sasa | 422/33 |
| 4,642,165 | 2/1987 | Bier | 422/28 |
| 4,648,978 | 3/1987 | Makinen et al. | 422/28 |
| 4,687,635 | 8/1987 | Kaehler et al. | 422/26 |
| 4,697,854 | 10/1987 | Lunsford | 312/223 |
| 4,712,657 | 12/1987 | Myers | 190/28 |
| 4,730,729 | 3/1988 | Monch | 422/300 |
| 4,731,222 | 3/1988 | Kravolic et al. | 422/37 |
| 4,732,187 | 3/1988 | Monch | 422/300 |
| 4,744,951 | 5/1988 | Cummings et al. | 422/28 |
| 4,748,007 | 5/1988 | Gaudion et al. | 422/300 |
| 4,752,444 | 6/1988 | Bowen et al. | 422/28 |
| 4,763,678 | 8/1988 | Ott | 134/171 |
| 4,764,351 | 8/1988 | Hennebert et al. | 422/292 |
| 4,770,851 | 9/1988 | Joslyn | 422/27 |
| 4,810,469 | 3/1989 | Masuhara | 422/26 |
| 4,824,644 | 4/1989 | Cox et al. | 422/300 |
| 4,843,867 | 7/1989 | Cummings | 422/111 |
| 4,844,052 | 7/1989 | Iwakoshi et al. | 128/6 |
| 4,862,872 | 9/1989 | Yabe et al. | 128/6 |
| 4,863,688 | 9/1989 | Schmidt et al. | 422/28 |
| 4,892,706 | 1/1990 | Kravolic et al. | 422/28 |
| 4,909,999 | 3/1990 | Cummings et al. | 422/298 |
| 4,923,522 | 5/1990 | Sowers | 134/22.1 |
| 4,935,371 | 6/1990 | Rickloff | 435/296 |
| 4,941,519 | 7/1990 | Sestak et al. | 141/22 |
| 4,943,414 | 7/1990 | Jacobs et al. | 422/28 |
| 4,952,370 | 8/1990 | Cummings et al. | 422/28 |
| 4,956,145 | 9/1990 | Cummings et al. | 422/28 |
| 4,973,449 | 11/1990 | Kolstad et al. | 422/27 |
| 4,990,087 | 2/1991 | De Rocchis et al. | 433/104 |
| 5,008,079 | 4/1991 | Wutzler et al. | 422/28 |
| 5,054,584 | 10/1991 | Hoffman | 433/104 |
| 5,057,283 | 10/1991 | Guggenheim et al. | 422/116 |
| 5,068,087 | 11/1991 | Childers | 422/26 |
| 5,137,689 | 8/1992 | Cantrell | 422/28 |
| 5,165,503 | 11/1992 | Hoffman | 433/114 |
| 5,225,160 | 7/1993 | Sanford et al. | 422/28 |

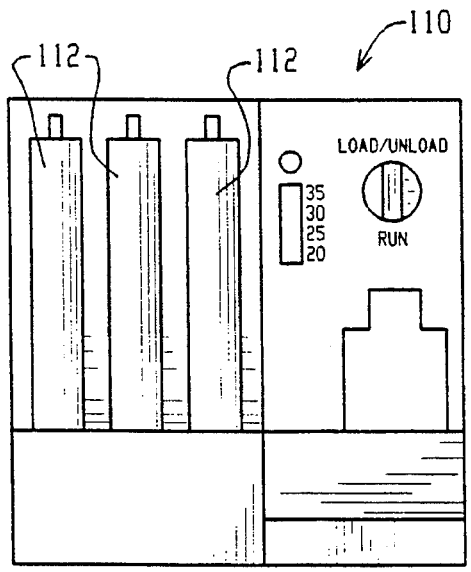
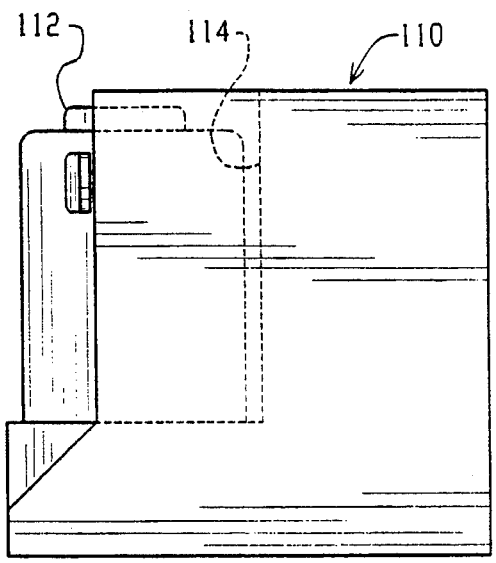
Fig. 6        Fig. 7
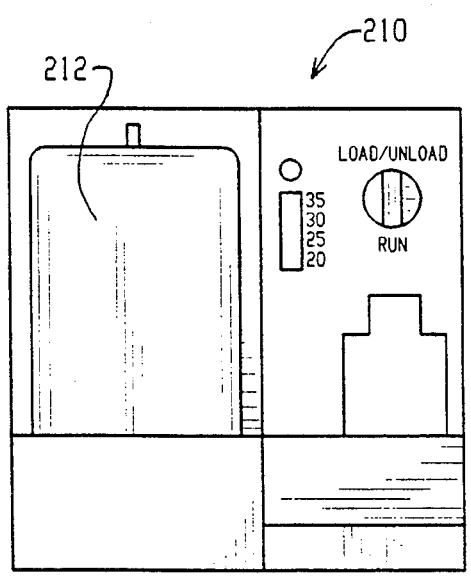
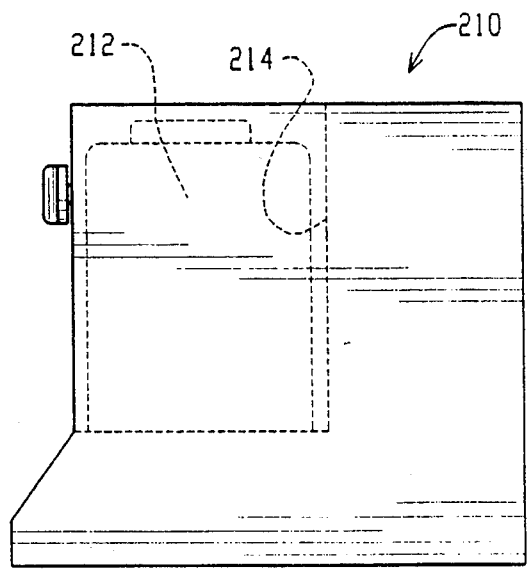
Fig. 8        Fig. 9

STERILIZATION APPARATUS AND METHOD FOR MULTICOMPONENT STERILANT

This is a divisional Ser. No. 08/279,688 filed on Jul. 25, 1994 now U.S. Pat. No. 5,492,672 which is a continuation of U.S. Ser. No. 07/851,415 filed Mar. 13, 1992 (now abandoned).

BACKGROUND OF THE INVENTION

1. Field of the Invention

The invention relates generally to sterilization methods and more particularly, to a method for sterilizing items using a multi-component vapor phase sterilant where one component is water.

2. Description of the Invention Background

Decontaminating instruments, such as air powered surgical or dental tools, or endoscopes having long, narrow lumens and other crevices, has always been a challenge. A variety of methods have been used to decontaminate these instruments. Examples include ethylene oxide, steam, formaldehyde and steam mixtures, dry heat, or liquid soaking. Instruments of this type, however, are very susceptible of damage from the high heat and/or moisture present in conventional decontamination systems.

In dentists' offices, where instruments must be used several times per day on different patients, it is important not only to sterilize the instruments between patients to prevent cross-contamination, but to do so quickly and economically without damaging the instrument.

A particularly troubling problem encountered in sterilizing instruments with long lumens or surface crevices is ensuring delivery of, and effective contact of, the sterilant with these hard to reach areas. Air pockets can form which create a shield of air against sterilant penetration.

It is known in steam sterilization systems to precondition the chamber to remove air. Preconditioning includes evacuation and pressurization of the chamber. U.S. Pat. Nos. 4,164,538; 4,335,071; and 4,687,635 are representative. Due to the damage that can be caused by the intense heat and moisture in steam sterilization, those methods are not suitable for sterilizing many instruments.

Several hydrogen peroxide vapor sterilization systems have been described in which the sterilant vapor is injected into an evacuated chamber. In one embodiment of a method disclosed in U.S. Pat. No. 4,956,145, a chamber is evacuated prior to the introduction of the hydrogen peroxide vapor to the closed chamber. Thereafter, intermittent make-up injections are made in variable amounts to maintain the concentration of the sterilant vapor in the chamber at a level below the saturation limit immediately following each such injection. The chamber is sealed throughout the cycle. One reason for the variable amounts of the make-up injections is the increase in relative humidity as the process proceeds.

In U.S. Pat. No. 4,909,999, a method is disclosed wherein hydrogen peroxide vapor is drawn into and through a chamber in a continuous flow-through sterilization cycle in which air is used as a carrier. The ambient air is drawn from the chamber prior to the introduction of the sterilant vapor-laden air flow.

None of these references focuses on the problems inherent in sterilizing instruments having long narrow lumens. There is a need for a sterilization method which will ensure contact between the sterilant and the hard to reach lumens and crevices of medical, surgical and dental tools. There is a further need for an economical low temperature sterilization method that will not damage the tools, that is not labor intensive and is not time consuming.

Finally, there is a need for a sterilization method that can be operated in an office setting without the risk of exposing personnel to hazardous chemical sterilants residues.

BRIEF SUMMARY OF THE INVENTION

The present invention provides a sterilization method which includes the steps of reducing the pressure in the chamber to a first subatmospheric level, injecting sterilant vapor into the chamber for a first period of time sufficient for elevating the pressure therein to a second subatmospheric level and permitting the sterilant vapor to permeate the chamber. Thereafter, sterilant vapor is flowed into the chamber for a second period of time sufficient for elevating the pressure therein to a third subatmospheric level. The method proceeds by flowing sterilant vapor into, through and out of the chamber for a third period of time sufficient to maintain the pressure therein at a fourth subatmospheric level, which is preferably greater than or equal to the third subatmospheric level, then discontinuing the flow of sterilant vapor into, through and out of the chamber to hold the sterilant vapor therein at about the fourth level for a fourth period of time sufficient to permit the sterilant vapor to permeate the chamber and come into effective contact with items to be sterilized. The latter steps of flowing sterilant and discontinuing the flow of sterilant are successively repeated in an alternating fashion a plurality of times until sterilization of goods in the chamber is achieved.

Where the goods to be sterilized include items having at least two open ends and a fluid flow path between the open ends, the method may also include fluidly coupling one end of each item to either the exhaust port or the inlet port of the chamber land flowing sterilant vapor through the fluid flow paths of each item and out the exhaust port. Depending on the type of items to be sterilized, the method may include the step of warming the items prior to reducing the pressure in the chamber to the first subatmospheric level. Warm air is drawn through the chamber as well as around and/or through the items during this warming phase.

The invention also provides an apparatus for sterilizing items having at least two open ends and a fluid flow path between the ends. The apparatus is particularly well suited for practicing the method of the present invention although other sterilization methods may be used. The apparatus includes a chamber having an inlet port and an outlet or exhaust port, and manifold means fluidly coupled to either the exhaust port or the inlet port. The manifold means has a plurality of seats for fluid connection to the fluid flow paths of a plurality of items. Means are provided for creating a negative pressure differential downstream of the exhaust port. The apparatus also includes, upstream of the inlet port, a source of liquid sterilant, means for vaporizing the liquid sterilant, valve means intermediate the liquid source and the vaporizing means for pulsing successive increments of the liquid sterilant into the vaporizing means, fluid connection means for fluidly connecting all of the foregoing and an airflow path through the vaporizing means and that portion of the fluid connection means from the vaporizing means to the chamber.

Items to be sterilized that have air turbines or motors are coupled to the manifold since the sterilant flow will operate the turbine or motor during the sterilization phase thereby exposing all surfaces to the sterilant. Sterilant flows through the chamber and around and through the devices to be sterilized once and is then discharged through a catalytic converter. The same sterilant is not recirculated through the devices and chamber a second time.

Since the chamber and devices are in a vacuum when the sterilant is present, penetration into crevices and dead end lumens is enhanced. Fewer air molecules are present to hinder diffusion of the sterilant. All air entering the unit is HEPA filtered to remove any particles which might catalytically destroy the sterilant when it is in the sterilization chamber.

An embodiment is provided having individual cassettes or modules for releasable connection to the fluid flow lines of the apparatus. The cassettes are useful for holding endoscopes in a manner similar to that for holding handpieces.

BRIEF DESCRIPTION OF THE DRAWINGS

The present invention can be better understood by reference to the drawings wherein like elements have like numbers and wherein:

FIG. 6 is a front elevational view of a sterilizer of the present invention wherein multiple sterilization cassettes may be used;

FIG. 7 is a side elevational view of the sterilizer of FIG. 6;

FIG. 8 is a front elevational view of another embodiment of the sterilizer of the present invention wherein a single cassette may be used;

FIG. 9 is a side elevational view of the sterilizer of FIG. 8;

DETAILED DESCRIPTION OF A PREFERRED EMBODIMENT

FIGS. 1–3 and 5 illustrate three embodiments of the sterilization cycle of the present invention. The cycle is designed for use with a multi-component vapor wherein one component is preferably water. A preferred sterilant is hydrogen peroxide vapor generated from an aqueous solution of 30 wt % hydrogen peroxide. Hydrogen peroxide in other concentrations and peracetic acid would also function as suitable sterilants for practicing the method of the present invention.

Figure 4:
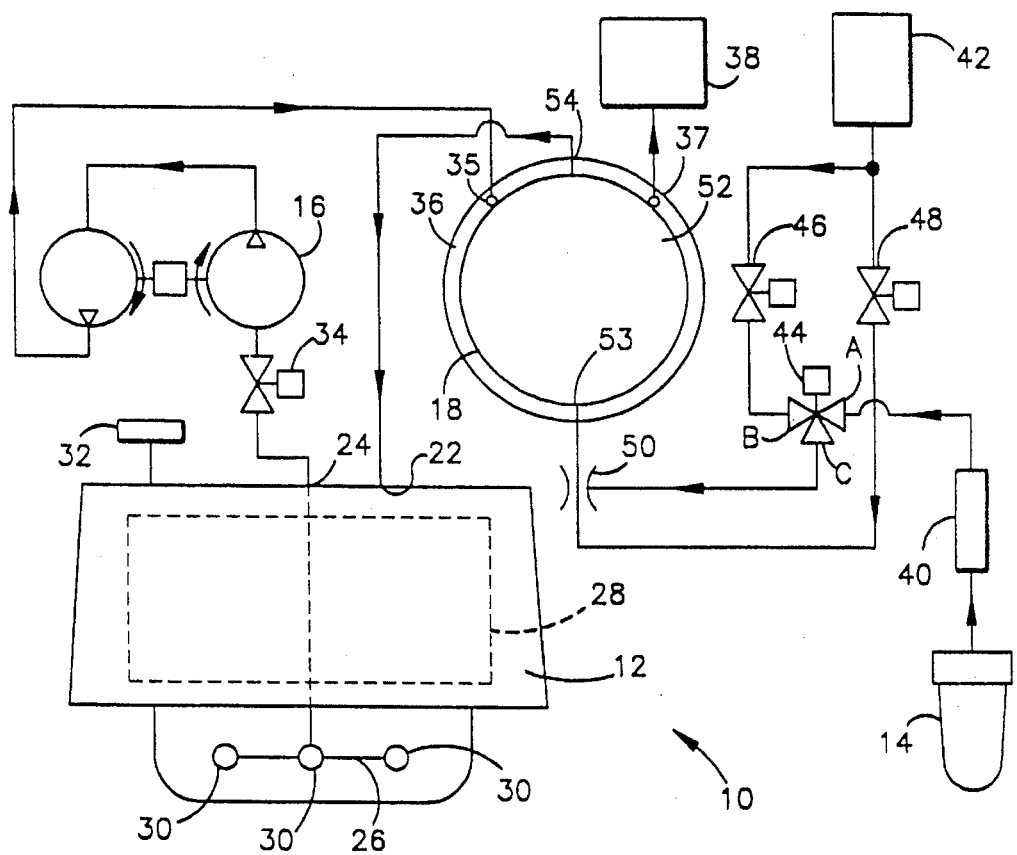
FIG. 4 is a schematic diagram of a sterilizer in which the method of the present invention can be practiced.

FIG. 4 illustrates a sterilizer 10 in which the method of the present invention can be practiced. Sterilizer 10 includes generally, a chamber 12, a source of liquid sterilant 14, a vacuum pump 16, a vaporizer 52 and four valves 34, 44, 46 and 48.

The sterilization chamber 12 includes an inlet port 22 and an outlet port 24. A manifold 26 fluidly connects the outlet port 24 to a plurality of handpiece connectors 30 (three are shown) within the chamber 12. A medical, dental or surgical tool or handpiece having at least two open ends and a fluid flow path therebetween is mounted or seated on each connector 30 for sterilization.

Figure 14:
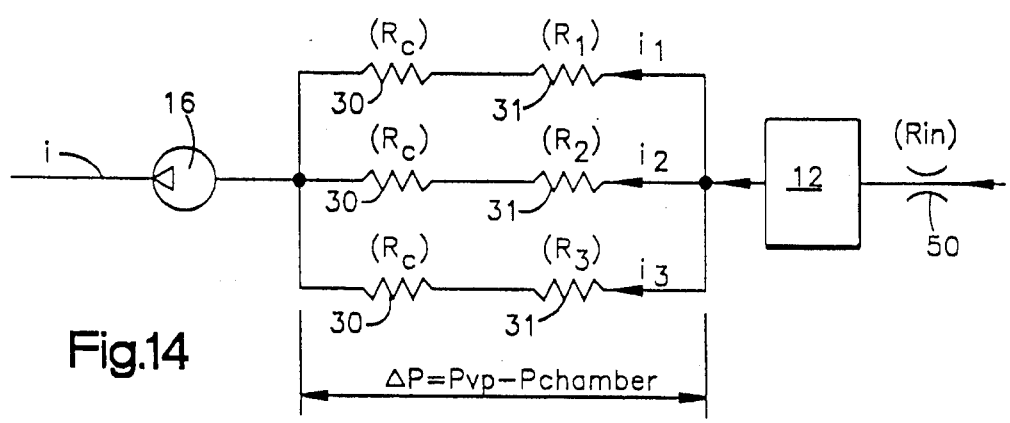
FIG. 14 is a schematic of the sterilizer of the present invention illustrating sterilant flows and pressures.

The orifice of each handpiece connector 30 is sized to provide a flow resistance which is greater than, or equal to, the flow resistance of the handpiece (or other instrument). This will distribute the flow through the handpiece and connector so that each individual connector experiences about the same flow. The flow resistance ensures that at least 20% of the total flow but not more than 50% of the total flow will pass through each connector 30 regardless of how many handpieces are being processed or where they are placed. In any event, there will be sufficient flow to ensure that sterilant reaches and flows through the handpieces when seated on the connectors 30. As shown in FIG. 14, assuming three connector orifices 30 with equal flow resistance $R_c$ which can each accept handpieces 31, or other instruments, with flow resistance of $R_1$, $R_2$ and $R_3$ are connected in parallel. As such and assuming that the flow restrictor 50 has a flow resistance $R_{in}$, the following will apply:

Total flow $i = i_1 + i_2 + i_3$ $$\text{Flow } i_1 = \frac{(R_c + R_2)(R_c + R_3)}{(R_c + R_1)(R_c + R_2) + (R_c + R_2)(R_c + R_3) + (R_c + R_1)(R_c + R_3)} i$$

$$i_2 = \frac{(R_c + R_1)(R_c + R_3)}{(R_c + R_1)(R_c + R_2) + (R_c + R_2)(R_c + R_3) + (R_c + R_1)(R_c + R_3)} i$$

$$i_3 = \frac{(R_c + R_1)(R_c + R_2)}{(R_c + R_1)(R_c + R_2) + (R_c + R_2)(R_c + R_3) + (R_c + R_1)(R_c + R_3)} i$$

where: $R_c$ = flow resistance of each connector 30

$R_{in}$ = flow resistance of flow restrictor 50

$\Delta P = P_{VP-Pchamber}$ i = total flow.

$P_{Chamber\ 12} = i\ R_{in}$ $P_{VP} = (i\ R_{in} \Delta P) .$= Pressure to Vacuum Pump Inlet If $R_c \approx R_1 \approx R_2 \approx R_3$, these equations produce the following:

|  | Number of Handpieces | | | |
| --- | --- | --- | --- | --- |
|  | 0 | 1 | 2 | 3 |
| $R_1$ | 0 | 0 | 0 | 1 |
| $R_2$ | 0 | 0 | 1 | 1 |
| $R_3$ | 0 | 1 | 1 | 1 |
| $i_1$ | ⅓ i | ⅔ i | ½ i | ⅓ i |
| $i_2$ | ⅓ i | ⅔ i | ¼ i | ⅓ i |
| $i_3$ | ⅓ i | ⅓ i | ¼ i | ⅓ i |
| $P_{chamber}$ | $-i\,R_{in}$ | $-i\,R_{in}$ | $-i\,R_{in}$ | $-i\,R_{in}$ |
| $\Delta P$ | ⅓ i $R_c$ | ⅔ i $R_c$ | ½ i $R_c$ | ⅔ i $R_c$ |
| $P_{VP}$ | $-i(R_{in} + ⅓ R_c)$ | $-i(R_{in} + ⅔ R_c)$ | $-i(R_{in} + ½ R_c)$ | $-i(R_{in} + ⅔ R_c)$ |

The chamber 12 pressure (vacuum) is a constant since the fixed displacement vacuum pump 16 will produce a constant total flow i. The pressure drop across the handpieces 31 will vary as will the individual flow rates; however, the maximum flow will never exceed ½ i and the minimum flow will never be less than ⅕ i. (Note: connection orifice flow resistance values where $R_c = R_1, R_2$ & $R_3$ will produce flows where $i_1 = i_2 = i_3 = ⅓$ i).

It has been found that for an 8.3 liter chamber, a 1/16 inch diameter orifice compensates well. Alternatively, in-line flow control devices (not shown), such as a process relief valve pressure compensated flow control or any other suitable flow control device, can be used to compensate for the variations in pressure drop across in the handpieces 31 and connector 30.

The chamber 12 also includes a heater 28 and any suitable known temperature and pressure sensors, designated collectively herein as 32. A valve 34 is positioned in the exhaust line between outlet port 24 and pump 16. The outlet end of pump 16 is fluidly connected via suitable conduit to the inlet 35 of a catalytic converter 36. The converter 36 houses a plurality of spheres which define a low flow-resistant tortuous path having a high surface area for degradation of the sterilant. When the sterilant is hydrogen peroxide vapor, the spheres are preferably coated with, or made entirely of, copper or some other material known to catalytically degrade hydrogen peroxide. The outlet 37 of the catalytic converter 36 is fluidly connected to an acoustical exhaust outlet filter 38.

The pump 16, which is preferably a two stage oil less vacuum pump, draws the liquid sterilant from its source 14 through a particulate filter 40 to port A of a three-way injection valve 44. Valve 44, when opened, is continuously pulsed alternately with air injector valve 46 so that discrete increments of liquid, approximating a steady stream, pass through path A→C of valve 44. Air is drawn through a HEPA filter 42, either through air injector valve 46 to port B and path B→C of valve 44 or through an air break solenoid valve 48 directly into the inlet 53 of a vaporization chamber 52, bypassing valve 44. A flow restrictor (venturi) 50 is provided in-line, upstream of inlet 53 so that the air or the air and sterilant mixture passes through flow restrictor 50 to inlet 53 of the vaporization chamber or vaporizer 52.

The vaporization chamber 52 includes a surface heated by any suitable heater, such as an electric band heater 18. The temperature of the vaporization chamber 52 when used to vaporize hydrogen peroxide is about 60°–150° C. (140°–302° F.). When path A→C of valve 44 is momentarily pulsed open, liquid sterilant is drawn in continuous but intermittent pulses or increments into the vaporization chamber 52 along with air. The liquid increments are vaporized and carried by the air through outlet 54 of vaporization chamber 52 via any suitable conduit to the inlet 22 of the sterilization chamber 12. This conduit may also contain an absolute filter (not shown). The vapor will sterilize the filter in place as it passes through. This conduit and filter can be insulated and/or heated to prevent condensation of sterilant prior to delivery to the sterilization chamber 12. The vaporization chamber 52 and converter 36 may be separate units or may be housed together in a single unit as described in U.S. Pat. No. 4,909,999, the relevant portions of which are incorporated herein by reference.

In a first alternate embodiment of the apparatus a detachable cassette may be inserted into, or substituted for, the chamber. In a second alternative embodiment of the apparatus of the present invention, shown in FIGS. 6–13, the chamber 12 may be adapted to receive a plurality of individual cassettes, 112, 212 or 312. The cassettes may hold one or more instruments and can be independently loaded, sterilized, aerated and unloaded. The instruments or goods to be sterilized can be stored in the cassettes until ready for use or removed promptly to permit reuse of the cassette. Each individual cassette would form the "chamber" or enclosure in which sterilization occurs. The cassette "chambers" are fluidly coupled to the inlet and exhaust ports 22 and 24. The cassettes may be received and housed in chamber 12 or its equivalent structure during sterilization. In that instance, the cassettes need not conform to the structural standards required of a chamber which must withstand the physical stress of vacuum and pressurization. The cassettes can be made of lighter weight material because they will be housed in the sturdier chamber 12 during the sterilization process. Alternatively, the cassettes can themselves function as a complete but removable sterilization chamber. In other words, the cassettes need not be inserted into another chamber but would themselves form the chamber, as shown for example in FIG. 10. In that instance, the cassettes would have to conform to every structural safeguard of a conventional chamber which will be subjected to vacuum and pressure conditions. The structural requirements for such chambers are well known in the art and do not form part of this invention.

Figure 10:
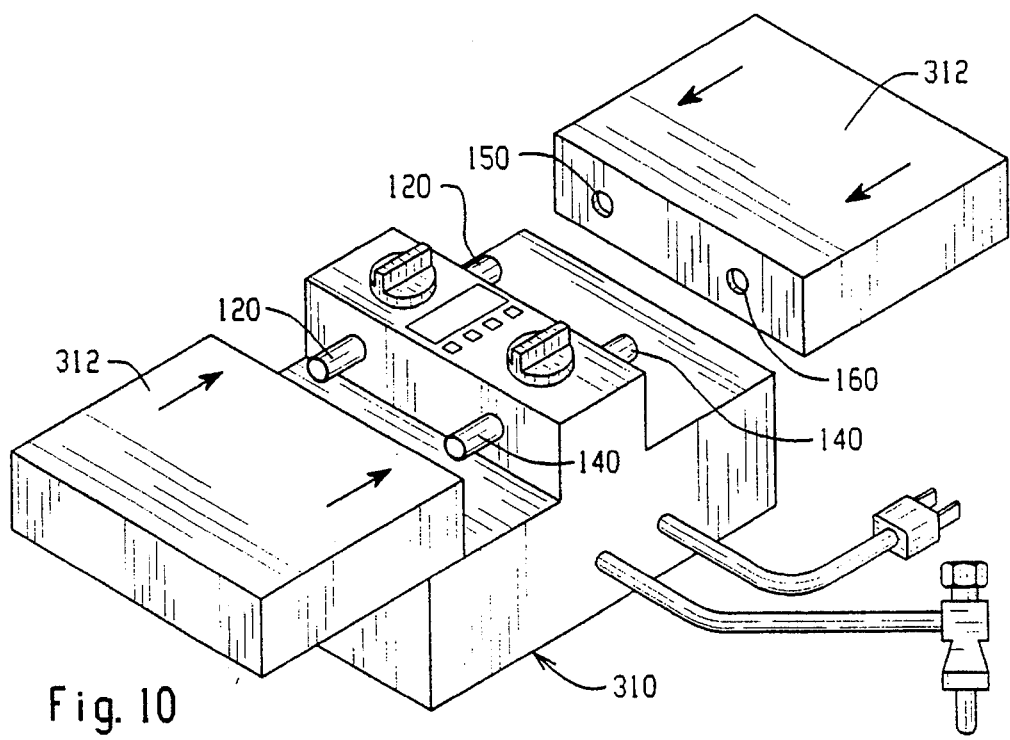
FIG. 10 is a perspective assembly view of an embodiment of the sterilizer of the present invention that utilizes cassettes as sterilization chambers.

Referring to FIGS. 6 and 7, an apparatus 110 is shown which will accommodate three cassettes 112. Each cassette 112 can slide into corresponding openings 114 located in the front of the apparatus 110. FIGS. 8 and 9 show a similar apparatus 210 having a larger opening 214 to receive a single, larger cassette 212. FIG. 10 shows a portable apparatus 310 adapted to receive two cassettes 312. In each of those embodiments, the cassettes 112, 212 or 312 are fluidly coupled to the respective apparatus 110, 210 or 310, in the same manner, e.g., as shown in FIG. 11.

Figure 11:
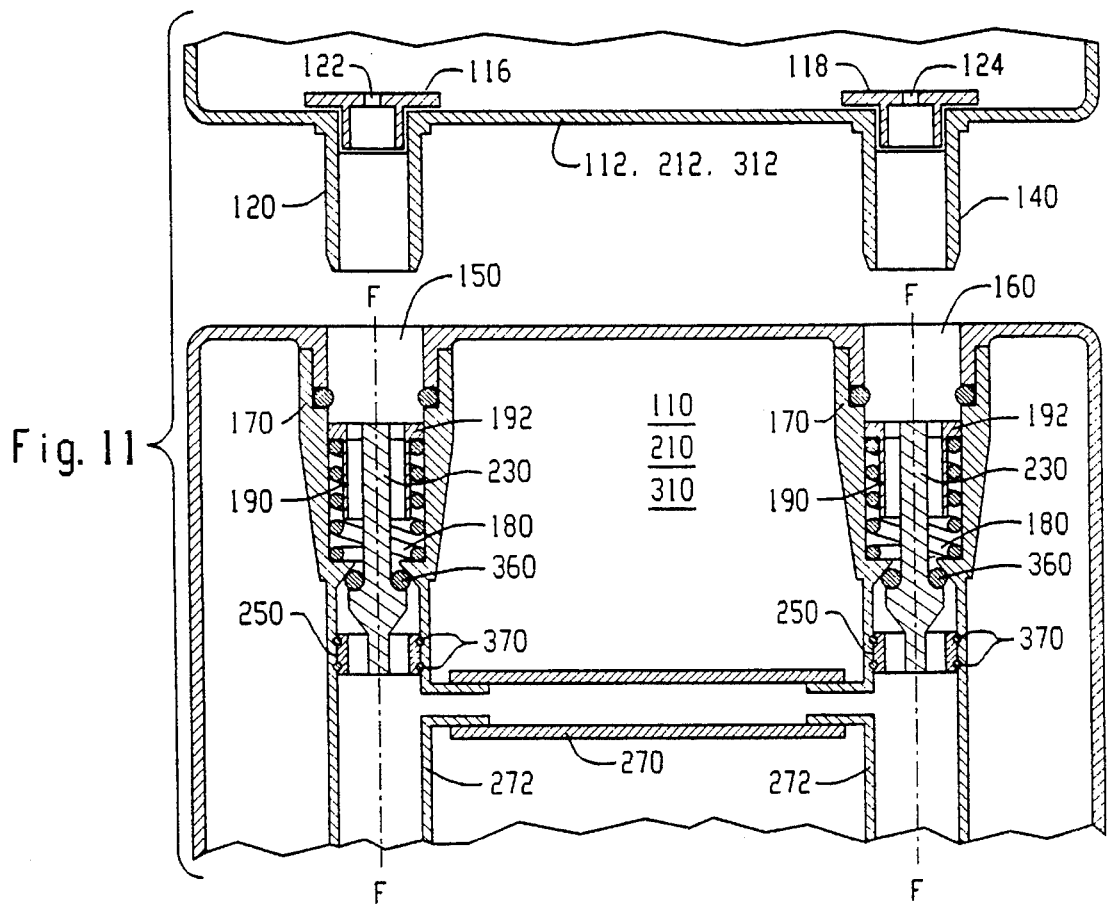
FIG. 11 is a cross-sectional assembly view of the sterilizer and cassettes of FIGS. 6–10.

FIG. 11 illustrates a cassette 112, 212 or 312, having two male extensions 120, 140. Extension 120 includes a sealing member 116 having an inlet orifice 122. Extension 140 includes a sealing member 118 having an outlet orifice 124.

Each orifice 122, 124 opens into the cassette 112, 212 or 312. FIG. 11 also illustrates female channels 150 and 160 which are sized to receive male extensions 120 and 140, respectively, to fluidly connect the cassettes to the respective apparatus 110, 210 or 310. Each channel 150, 160 includes seals 170, 360, 370, preferably o-ring seals, a spring member 180, a receiving member 190 for slidably receiving the ends of the male extensions 120, 140, an actuation member 230 and a blocking member 250. Each actuation member 230 extends through the longitudinal axis F-F of the corresponding receiving member 190 and, with the receiving member 190, defines an annular space for receiving the ends of the extension 120, 140. The receiving member 190, actuation member 230 and blocking member 250 are operatively connected so that they move in unison when the receiving member is moved deeper into the channel 150 or 160. A bypass conduit 270 fluidly connects the channels 150 and 160 via channels 272.

When a cassette 112, for example, is connected to the apparatus 110, the extensions 120, 140 are inserted into the channels 150, 160, respectively. The ends of the extensions 120, 140 slide into the channels 150 and 160 to abut the flanges 192 of the receiving members 190 and push the receiving members 190 deeper into the channels 150, 160. The actuation members 230 move with the receiving members 190 and in turn move the blocking members 250 into position over the channels 272 of the bypass conduit 270 to block the fluid connection between the channels 150 and 160.

The cassette 112 is thus fluidly connected to the fluid flow lines of the apparatus 110, 210, 310. Channel 150, for example would fluidly connect the cassette, through conduit member 120 and orifice 122, to inlet port 22. A sterilant vapor flow from the vaporization chamber 52 would be directed through channel 150 to orifice 122 into the cassette. Channel 160 would fluidly connect the cassette 112, through extension member 140 and orifice 124, to port 24 to exhaust the cassette. The extensions 120, 140 are held firmly in channels 150, 160. Additional means such as, for example, clamps (not shown) can be provided, however, to lock the cassette into position to maintain the fluid connections during operation and to prevent inadvertent removal of a cassette during processing.

As stated, there may be one, two, three or more cassettes and means for fluidly connecting the cassettes to the fluid flow path of the apparatus. It will be understood that each cassette has a pair of extensions 120, 140 and the apparatus for which it is adapted has one, two or more pairs of fluid connection channels 150, 160 to receive the extension pairs 120, 140 of the corresponding cassettes.

When a cassette 112, 212 or 312 is removed from the apparatus, spring members 180 urge the receiving members 190, and with it, the blocking members 250 outwardly, away from the bypass conduits 270. The bypass conduit 270 then fluidly joins the channels 150, 160 of a pair so that any flow directed to one channel will pass through the bypass conduit 270 to the other channel of the pair to direct the fluid flow to exhaust. The seals 360 and 370 prevent such flow from leaking from the corresponding channels 150 and 160 to the outside. Flow might continue in an embodiment suitable for accommodating several cassettes. If all of the available pairs of connection channels 150 and 160 are not fluidly joined to a cassette, and a sterilization process is run, the unused pairs of connection channels 150 and 160 are blocked in the above-described manner.

In embodiments having two or more cassettes, the ports 22, 24 of the apparatus are joined to manifolds having the necessary complement of connections to fluidly connect each cassette to the fluid flow lines of the apparatus. Each manifold connection is preferably equipped with its own valves to individually control vapor/air flow into each cassette and the exhaust applied to each cassette. Such vapor/air flow valves would replace the three-way valve 44 shown in FIG. 4. Individual exhaust valves would replace the valve 34 shown in FIG. 4.

Figure 12:
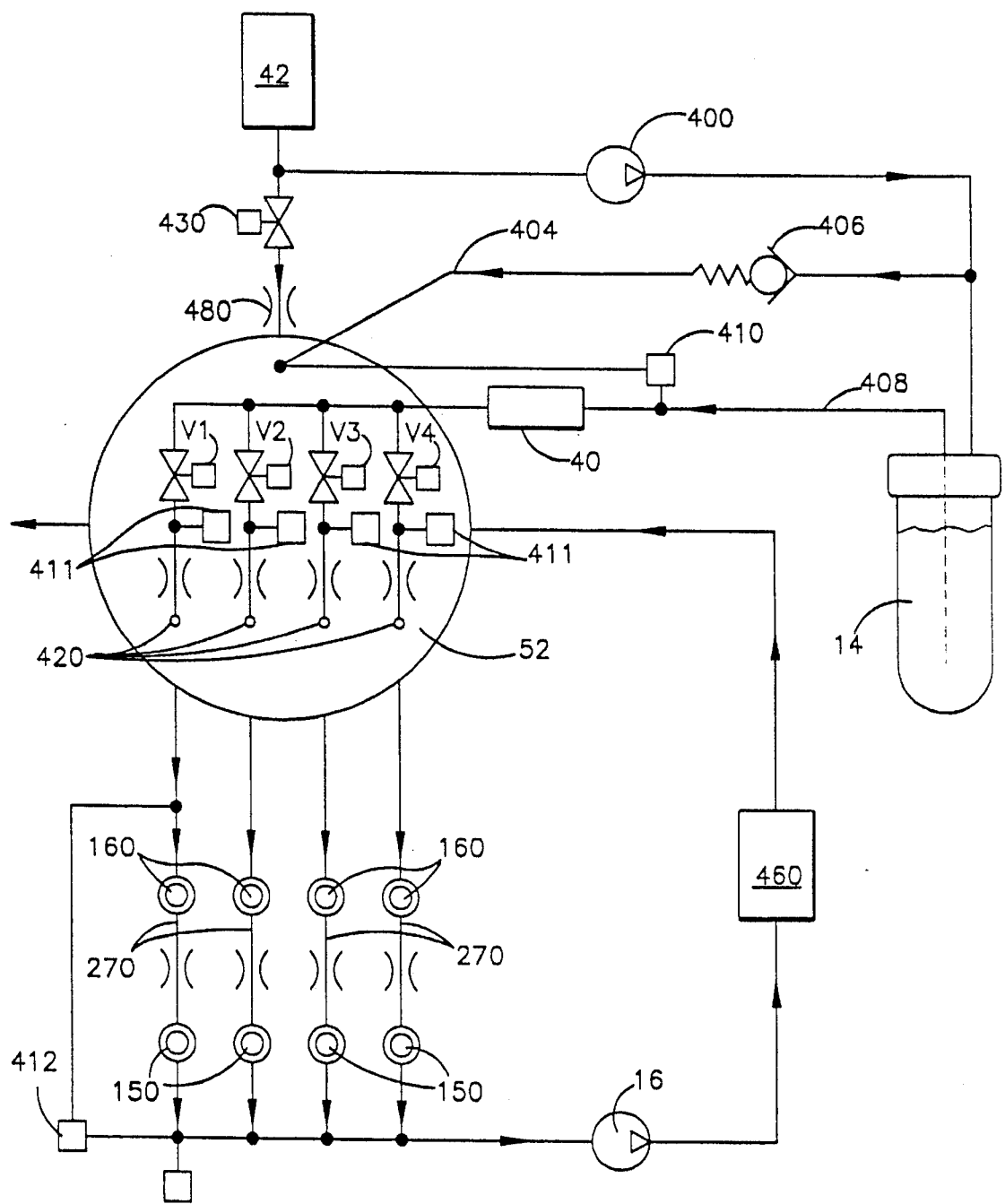
FIG. 12 is a schematic diagram of a sterilizer in which the method of the present invention can be practiced with one to four cassettes.
Figure 13:
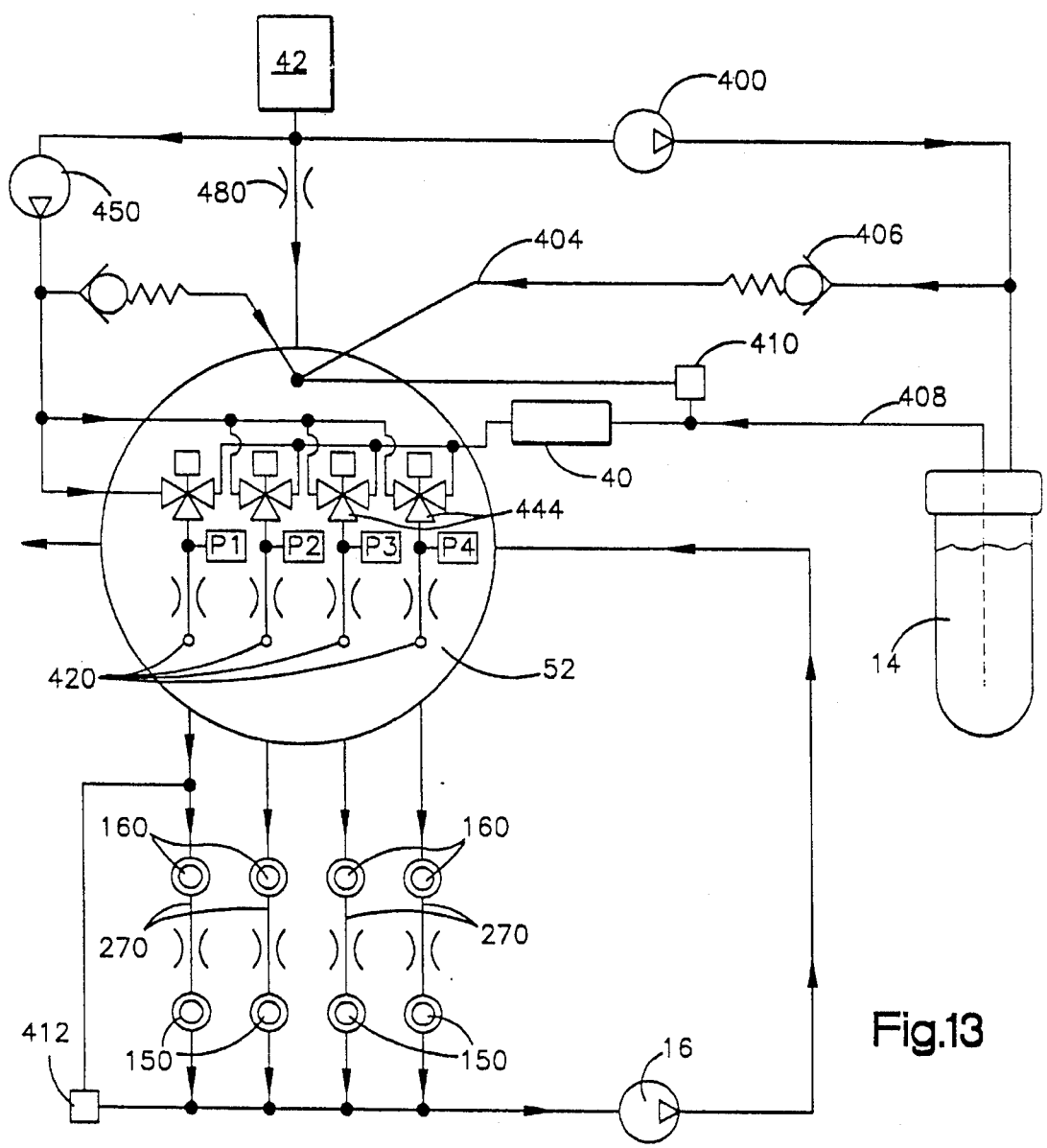
FIG. 13 is a schematic diagram of an alternate embodiment of a sterilizer in which the method of the present invention can be practiced with one to four cassettes.

Referring to FIGS. 12 and 13, schematic diagrams are provided which show alternative arrangements for providing individually controlled flow to the cassettes. As shown in FIG. 12, a single vacuum pump 16 is used to create the flow through all four independent cassettes (not shown). The connection channels 150, 160 and bypass conduits 270 are shown. The air exiting the vacuum pump 16 is preferably filtered through an air outlet filter 460 before it re-enters the vaporization chamber 52. Solenoid injection valves $V_1$, $V_2$, $V_3$ and $V_4$ are controlled individually so that each circuit can independently be in either the sterilize phase or the aerate phase. Injection control can be controlled by four independent systems as described for the apparatus shown in FIG. 4. Alternatively, a single air pump 400 and differential pressure switches 410 and 411 are used to control the liquid sterilant injection. More specifically, air pump 400 draws air through HEPA filter 42 and pumps it into the sterilant source 14 through a suitable conduit as shown in FIG. 12. It will be appreciated that as air is pumped into the sterilant source 14, the liquid sterilant is caused to flow through a supply conduit 408 to a particulate filter 40 and then to the valves V1, V2, V3 and V4. Air pump 400 also discharge excess air flow into the vaporization chamber 52 through a suitable conduit 404. An in-line relief valve 406 is preferably provided to provide a controlled air pressure to the sterilant source 14. Pressure switches 410 and 411 communicate with the vaporization chamber 52 and the sterilant supply conduit 408 to insure that the proper mix of air and sterilant enters the vaporization chamber 52. Four separate, but equal injection orifices 420, are also employed.

The channels 150, 160 in the cassettes can be used to produce similar pressure differentials across all cassettes resulting in a fairly uniform distribution of air flow. A pressure differential switch 412 is also preferably used to measure the pressure differential existing across the channels 150 and 160 of the cassettes.

The embodiment shown in FIG. 12 employs a vacuum valve 430 and pressure switches 411 to check for plugged injectors. For this check to be utilized, the entire sterilizer must be evacuated somewhat. Thus, it is preferably done when no sterilization cycles are in progress. Vacuum valve 430 also functions in a manner similar to valve 48 in FIG. 4.

Optional restriction orifice 480 is used to regulate the pressure within the vaporizer and cassettes. The embodiment of FIG. 13 employs a second air pump 450 to independently check for clogged injectors or injection orifices 420, to independently purge liquid sterilant from each injector 420 at the end of a cycle and to urge individual sterilant increments into the vaporizer 52 when valves 444 are pulsed. The embodiment shown in FIG. 13 eliminates an outlet air filter and a chamber vacuum switch.

Figure 1:
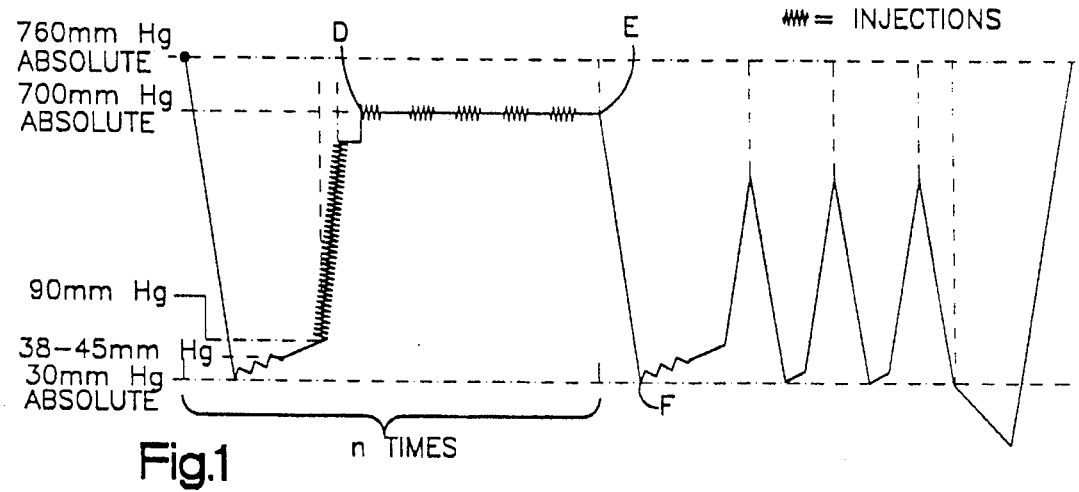
FIG. 1 is a graph of one embodiment of the sterilization cycle of the present invention.
Figure 3:
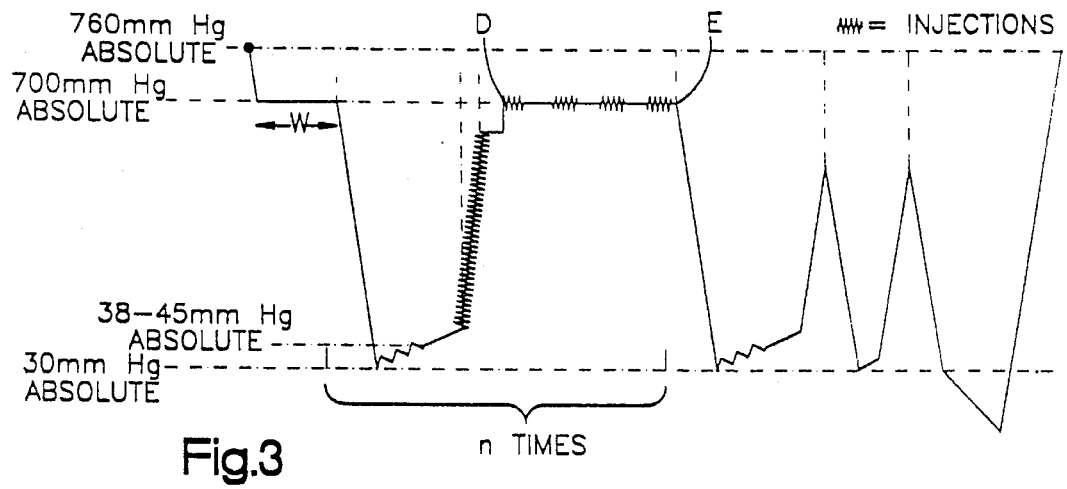
FIG. 3 is a graph of a second embodiment of the sterilization cycle of the present invention.
Figure 5:
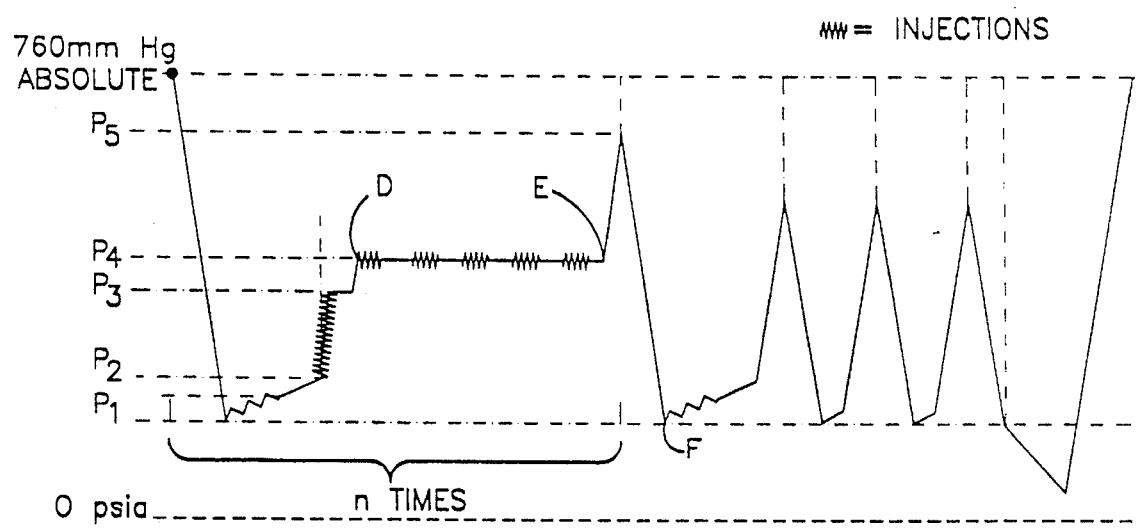
FIG. 5 is a graph of a third embodiment of the sterilization cycle of the present invention.

The sterilization cycles shown in FIGS. 1 and 3 are very similar. Portions of the cycle of FIG. 5 are run at lower pressure levels than are typical for the cycles of FIGS. 1 and 3. The cycle of FIG. 1 is particularly useful for sterilizing high speed handpieces, dental burrs and other instruments sensitive to heat. The cycle of FIG. 3 is useful for sterilizing a broader range of instruments, including but not limited to high speed handpieces and dental burrs. In the cycle of FIG. 3, during phase W, the sterilization chamber 12 is preferably warmed by flowing air through valve 48 to the vaporization chamber 52 where it is warmed. The warm air is then drawn into the sterilization chamber 12, flowed through the sterilization chamber, over the instruments and through the lumens of those instruments coupled to the connectors 30 and then to outlet port 24. The warm air slightly warms the load prior to initiation of the sterilization cycle. The sterilization cycle is preferably run within a range between about room temperature to a temperature up to 50° C., and preferably at about 37° C. With increased sterilant injection at about 60°–70° C. the deleterious effect of the chemical sterilant on the materials is increased without correspondingly significant gain in sterilization efficacy. When hydrogen peroxide vapor is the sterilant, the vapor begins to degrade faster at higher temperatures. Lower temperatures without correspondingly lower sterilant injection rate can lead to condensation of the sterilant vapor. Condensation is avoided to obtain a wider range of material compatibility. Thus, the sterilization temperature should be above the condensation temperature of the sterilant.

In the embodiment of the cycle of the present invention, the instruments to be sterilized, if any, are placed in the sterilization chamber 12. If the sterilization chamber 12 is a freeze dryer it is likely that no instruments will be placed inside. Instruments with air turbines or motors and lumened instruments are mounted on the handpiece connectors 30. Endoscopes may be placed in cassettes, as described, if that embodiment is used and the cassettes are connected to the fluid flow lines of the apparatus as described. The process will be described with reference to the chamber 12 but when cassettes are used, the environment attributed to channel 12 would be present in the cassettes as well if coupled to the apparatus. Other types of instruments are placed according to accepted sterilization practices.

Following the warming phase, if used, a vacuum is drawn within the sterilization chamber 12 (or cassettes, if used) to below 0.6 psia (30 mm Hg absolute) as shown more clearly in FIG. 2. The substantial absence of air and other gases or vapors from the sterilization chamber 12 enhances the ability of the sterilant vapor to penetrate crevices and lumens when it is injected. Following this vacuum draw to a first subatmospheric pressure level, injection phases occur a number of times (n) wherein, in each, the chamber pressure is raised to second, third and fourth subatmospheric levels, and optionally a fifth level (see FIG. 5) n times, during the process. There are preferably at least two phases (n) and, more preferably, four or six phases (n) in the process. Air is alternately drawn through air injector valve 46 and port B→C of valve 44 with sterilant which is drawn from source 14 through port A→C of valve 44 to the vaporization chamber 52. The vapor pressure of the sterilant carries it to inlet 22 (due to the presence of the vacuum) where it is introduced to the sterilization chamber 12 over a time interval lasting for about 10 to 60 seconds depending upon the device being sterilized and the size of the sterilization chamber 12. The injections raise the sterilization chamber 12 pressure to a second subatmospheric pressure level about 8–15 mm Hg (absolute) higher than the initial vacuum level (e.g. to 38–45 mm Hg (absolute) in FIG. 2). Optionally, the amount (weight) of sterilant injected can be monitored and controlled. The pressure rise is monitored by sensor 32. The injection of approximately 0.2 grams of 30 wt % hydrogen peroxide liquid into an 8.3 liter sterilization chamber 12 yields a momentary hydrogen peroxide vapor concentration of 7.2 mg per liter. A vapor concentration sensor can be used to monitor this concentration. There is a brief hold period, lasting about 15–20 seconds, during which air injector valve 46 is opened to provide a slow air break. Exhaust valve 34 is closed. The pressure in chamber 12 rises to about 90 mm Hg (absolute). Then air laden with sterilant vapor is injected into the sterilization chamber 12 in nearly continuous pulses. Decreasing amounts of sterilant vapor are drawn in during this period because as the pressure in the chamber 12 and sterilant injector valve 44 rises, the pressure differential across the air injector valve 16 decreases. The force drawing the vapor into the chamber 12 decreases so smaller amounts of vapor enter the chamber 12 as the pressure approaches the desired level. During this period, when the sterilant vapor pressure in the chamber 12 is increasing, the sterilant remains in effective contact with the exterior of the goods in the sterilization chamber 12.

As shown in the Figures the injection pulses continue, for about ten seconds, until the sterilant vapor concentration is raised to the desired third subatmospheric pressure level (for example, preferably between about 600 and 700 mm Hg absolute). The addition of sterilant pulses has been found to enhance sterilant penetration. When the pressure in chamber 12 rises to near the desired third subatmospheric pressure level as monitored by sensor 32, there is a second hold period for about ten more seconds. Then, at point D on the cycle graphs, valves 46 and 34 are alternately pulsed open for about another ten seconds.

At point D on the cycle graphs, the flow-through sterilization phase of the cycle begins. It has been shown that it is during this part of the cycle that sterilization of the long lumens on the instruments actually occurs. During the flow-through sterilization phase, there are successive alternating sterilant injection periods and holding periods where the injections are discontinued. The pressure is maintained generally at a fourth subatmospheric pressure level at this stage. In the cycles of FIGS. 1 and 3, the fourth subatmospheric pressure level is preferably between about 700–760 mm Hg absolute. In one embodiment of the cycle, however, shown in FIG. 5, the fourth level can be much lower, for example at about 26 mm Hg absolute (½ psi vacuum). The other levels are also much lower. In the case where the sterilization pulses and hold periods are practiced at such low pressure levels, a fifth subatmospheric pressure pulse is added at about point E to reduce the humidity in the chamber by a factor of at least ten when the chamber pressure is reduced to point F.

In one embodiment practiced in an 8.3 liter sterilization chamber, each injection and hold period lasts about ten seconds. The precise duration may vary depending on such factors as sterilization chamber size, vapor concentration, air flow rate, load size and sterilization chamber pressure. There is preferably a complete air/vapor exchange five to six times per minute. The exchange is very rapid. A slower air exchange rate will likely result in a longer cycle time. The injection of 0.055 grams in a ten second period with a corresponding air flow of 1.1 SCFM in the slightly evacuated sterilization chamber (700 mm Hg absolute) produces a nominal hydrogen peroxide concentration of 3.18 mg per liter.

Cummings et al., U.S. Pat. No. 4,956,145, issued Sep. 11, 1990, the relevant portions of which are incorporated herein by reference, sets forth several Tables which show the concentration of hydrogen peroxide under various temperature and relative humidify conditions as well as the amounts of hydrogen peroxide vapor to inject to raise the sterilization chamber pressure to particular levels at different times during the process describe therein. Table II in the Cummings et al , '145 patent provide the saturation concentration based upon the chamber (vapor) temperature and chamber humidity, which must be corrected for vacuum operation.

The injection rate is calculated to produce a vapor concentration which is less than the saturation amount. Exceeding the saturation concentration (i.e. dew point conditions) will result in condensation.

The concentration produced by the sterilizer must be less than or equal to this saturation concentration C(sat).

$$\frac{\text{Injection Rate} \times .30 \text{ wt \%} \times 1000 \text{ mg/gram}}{\text{AIR FLOW}} \leq c(\text{sat})$$

If the air flow volume is measured at the inlet near filter 42 the volumetric air flow within the chamber must be corrected for temperature and pressure changes using the following equation which has been derived from the ideal gas laws:

$$\text{AIR FLOW} = \text{Inlet Flow} \times \frac{P_{inlet}}{P_{chamber}} \times \frac{T_{inlet}}{T_{chamber}}$$

In the cycle of FIG. 1, there are preferably five injection periods from points D to E, where n=4, each injection period followed by a static hold period. In the cycle of FIG. 3, there are preferably four injection periods from points D to E, where n= 6. Each injection period is followed by a static hold period, as in FIG. 1. The high flow injection periods quickly kill exposed areas in long lumens. The static hold periods permit sterilant vapor penetration in the crevices and hard to reach areas on both the outside and interior surfaces (including lumens) of the instruments. The high flow rate and subatmospheric conditions help push sterilant through the lumens to the end which have heretofore been the hardest areas to sterilize. In addition, the high flow rate maintains the desired concentration. The hold periods also permit some of the hydrogen peroxide sterilant to degrade.

During the static holding periods, the exhaust valve 34 and air break valve 48 are closed. During the injection periods, the exhaust valve 34 and air break valve 48 are open. Three way injection valve 44 and air injector valve 46 alternately pulse continuously whenever exhaust valve 34 is open, but are never continuously open.

When the valve 34 is open, pump 16 draws air through the open air break valve 48 and draws liquid sterilant through the particulate filter 40 and to path A→C of valve 44. As stated previously, valve 44 constantly pulses alternately with an injector valve 46 so that the liquid is nearly continuously delivered to the vaporizer in small increments. In the vaporization chamber 52, each increment is substantially instantaneously vaporized and drawn, in vapor form, through vaporizer outlet 54 to the inlet port 22 of sterilization chamber 12. The successive increments of liquid are delivered quickly so that there is almost a steady stream of such increments to the vaporization chamber 52 and almost a steady stream of vapor to sterilization chamber 12. For example, there are less than three seconds, and preferably less than one second, between successive increments. The incremental vaporization, however effectively overcomes the preferential vaporization of one component of a multi-component vapor over another component when one component is more volatile than the other. It thereby permits the vapor to maintain substantially the same relative concentrations of each of its components. The overall method of incremental vaporization is described in U.S. Patent No. RE 33007, reissued from U.S. Pat. No. 4,642,165.

At the conclusion of the alternating flow-through sterilization period, indicated as point E in FIGS. 1 and 3, the exhaust valve 34 is opened and the air break valve 48 and three-way injection valve 44 are closed. A vacuum is pulled in chamber 12 to below 30 mm Hg (absolute) to reduce humidity and the concentration of sterilant vapor in the chamber 12. Alternately, as shown in FIG. 5, air may be admitted at the end of the alternating flow-through sterilization period to further increase the chamber pressure to a fifth, preferably subatmospheric, pressure level. Then the vacuum is pulled as in the cycles of FIGS. 1 and 3. The ratio between the initial and final pressure in chamber 12 during evacuation equals the ratio between the initial and final chamber humidity and sterilant vapor concentrations. This ratio should be at least 10:1 to prevent humidity build-up between pulses which will result in condensation of sterilant. This will adversely affect sterilization, penetration and material compatibility.

In the cycle of FIGS. 1 and 5, a final deep vacuum injection pulse follows the final pulsing flow-through at point F. Valve 44 is alternately pulsed along with air injector valve 46 to draw liquid sterilant into the vaporization chamber 52 and vapor into the sterilization chamber 12 for a period of about 30 seconds. The vacuum in the chamber 12 remaining after the close of valve 34 provides the pressure differential necessary to draw the sterilant and/or air to the chamber 12. Path A→C of valve 44 is then closed and valve 46 and path B→C of valve 44 are opened to draw air into chamber 12 for about 15 seconds. Again, the vacuum level in the chamber 12 is sufficient to draw the air through valves 46 and 44 and through the vaporization chamber 52 to chamber 12. Air injector valve 46 is opened after valve 44 accepts an increment of liquid sterilant from path A→C of three-way valve 44 and is switched to path A→B of that valve. The air "slug" immediately pushes the liquid increment into the vaporization chamber 52. This alternating operation provides for quick pressure rise due to immediate vaporization thereby preventing over injection due to slow pressurized flow back to sensor 32. Air injection valve 46 is opened for 15–20 seconds before air break valve 48 is opened. After the air break valve 48 closes and pump 16 evacuates the chamber.

When the sensor 32 senses that the desired vacuum level has been achieved, the aeration phase begins. Any suitable aeration cycle can be employed. Two or three aeration pulses follow wherein air break valve 48 and exhaust valve 34 are opened for about four seconds, the air break valve 48 is closed while the exhaust valve 34 remains open to draw a vacuum in the chamber 12 to about 30 mm Hg, then the air injector valve 46 and path B→C of valve 44 are opened for about ten seconds. A similar aeration step is repeated, once or twice.

A leak test may be done in one of the aeration steps. During the leak test, the pressure in chamber 12 is drawn down to 30 mm Hg, all valves are closed for a period suitable for determining whether there is a pressure rise in the chamber 12, thereby indicating a leak. The final evacuation preferably continues for about forty seconds longer and pulls a greater vacuum than the previous evacuations. The longer evacuation is optimum for removal of residuals and clears any fogging occasioned by low temperatures and high relative humidity in chamber 12.

All air which enters the sterilizer 10 during the sterilization cycle must pass through HEPA filter 42. This prevents recontamination of the instruments that were sterilized during aerations. All gases and vapors that exit chamber 12 during its operation, pass through the converter 36. Hydrogen peroxide vapors are thereby reduced to water vapor and oxygen.

The pulsing vacuum flow sterilization cycle of the present invention combines the advantages of the flow-through sterilization cycles and static, hold cycles of prior systems. The combination offers the following advantages: maximum sterilant concentration regardless of ambient humidity without requiring an air dryer; lower chamber operating temperatures; and increased sterilization efficacy, especially during the pulsing hold periods, due to higher molecular impact frequency between the sterilant and the microorganisms (contained in the coupled devices) to be killed. The process is effective at low vapor concentrations. It has been calculated that during the flow-through phases, the sterilant is present at about 2,000–4,000 ppm. During the vacuum phases, the parts per million rise. While the actual amount (mass) of sterilant in the chamber 12 is high because the air and humidity are removed. As the process proceeds into the pulsing flow through phase the vacuum dilutes the humidity of the air carrier stream (because the air expands in volume when under vacuum) and draws it from the chamber. The advantages of vacuum operation can be explained by reference to the law of partial pressures which state that the total pressure of a mixture of gases equals the sum of the individual, or partial pressures.

$$D_{Air} = P_{Nitrogen} + P_{Oxygen} + P_{Water\ Vapor} + P_{Other\ gases} \quad \text{(Equation 1)}.$$

If during vacuum flow-through, each gases' pressure is reduced uniformly, a ratio of the Ideal Gas Law for vacuum versus non-vacuum operation would yield the following:

$$\frac{P_1 V_1}{P_2 V_2} = \frac{N_1 R T_1}{N_2 R T_2}, \quad \text{(Equation 2)}$$

where P= Partial water vapor pressure
V= $V_1=V_2$= Chamber volume
R= Ideal gas constant for water vapor
T= Chamber temperature
N= Moles of water vapor present.
Assuming T=$T_1$=$T_2$ a rearrangement of equation 2 will yield:

$$\frac{N_1/V}{N_2/V} = \frac{P_1}{P_2}. \quad \text{(Equation 3)}$$

Combining equation 3 with the assumption of uniform reduction in partial pressures yields the following:

$$\frac{N_1/V}{N_2/V} = \frac{P_{Chamber\ 1}}{P_{Chamber\ 2}}.$$

The ratio N/V for water vapor is essentially a measure of humidity. Thus, $$\frac{\text{Humidity 1}}{\text{Humidity 2}} = \frac{P_{Chamber\ 1}}{P_{Chamber\ 2}}.$$

Thus, operation at ½ atmosphere is equivalent to operation at 1 atmosphere but at half the humidity level. The vacuum flow-through operation can be viewed in a combination of ways. It maximizes the allowable sterilant concentration (for no condensation) at a given temperature. It also permits lower temperature operation for a given ambient temperature and humidity. In addition, there are fewer total molecules present in the chamber during the vacuum flow-through operation. Thus, the ratio of sterilant to other molecules is increased. This results in a higher molecular impact frequency between the sterilant and the biological entities. The result is increased sterilant efficacy.

Tests were done to compare the effectiveness of the combination vacuum flow-through sterilization process compared to a flow-through process or a static process alone. It has been found unexpectedly that the combination of flow-through sterilization with vacuum provides a more efficacious sterilization than is provided by the flow-through process or a static process alone. This is particularly true when applied to instruments and devices having long narrow lumens.

All tests were done in a sterilizer like that illustrated in FIG. 4 having a chamber made of ⅛ inch thick cast aluminum and a total internal volume of 8.3 liters. The sterilant used was 30 wt % hydrogen peroxide. The concentration and flow rate were similar for each test. The tests conformed to the Association of Official Analytical Chemists (AOAC) Sporicidal Test presently specified by the U.S. Environmental Protection Agency (EPA) to establish the minimum estimated contact time required for sterilization.

TABLE I

COMPARING THE EFFECTIVENESS OF A
FLOW-THROUGH ONLY CYCLE TO THE VACUUM/
FLOW-THROUGH CYCLE OF THE PRESENT INVENTION
IN STERILIZING SPORICIDAL TEST CARRIERS

| Cycle Description | Exposure Time, min. | # Positive Carriers/Tested |
|---|---|---|
| Flow-through | 10 | 14/16 |
| | 15 | 5/14 |
| | 20 | 4/7 |
| | 30 | 7/19 |
| Combination Vac/Flow-through | 16 | 0/120 |

The test results in Table I demonstrate that sterilant penetration and efficacy are improved with the use of the combination vacuum/flow-through cycle. A 16 minute (or less) exposure was required to consistently sterilize the AOAC carriers with the use of the vacuum/flow-through method while partial positives were still evident at 30 minutes for the flow-through cycle alone.

Another test protocol required by regulatory authorities to validate the minimum estimated contact time are direct product inoculation tests. The final exposure time according to the U.S. Food and Drug Administration (FDA) guidelines must equal the longer of a) the AOAC exposure time or b) double the inoculated product exposure time.

Brass lumens were inoculated with a greater than $10^6$ spore population. The brass pieces were directly connected to the orifices of the exhaust manifold in the sterilizer. The results of these tests are contained in Table II.

TABLE II

COMPARING THE EFFECTIVENESS OF A DEEP
VACUUM, STATIC CYCLE ONLY TO DEEP VACUUM/
FLOW-THROUGH EXPOSURES IN INACTIVATING
SPORES[a] DRIED IN LUMENS OF BRASS HEADPIECES
CONNECTED TO THE CHAMBER EXHAUST

| Cycle Description | Exposure Time, min. | Spore Survivors, CFU |
|---|---|---|
| 2-Deep vac injections with 4:00 min. hold, periods | 10 | >1000 |
| 1-Deep vac injection with a 5:00 min. flow-through | 9.5 | 35 |

[a]Initial spore population in lumens was >$10^6$

The results again demonstrate that significant improvement was obtained when the combination deep vacuum/flow-through cycle was used as compared to a deep vacuum/ static hold cycle alone. However, the combination cycle was unable to sterilize inoculated product in one half the AOAC exposure time which was experimentally determined to be 16 minutes or less.

Table III provides data showing that alternately starting and stopping the sterilant injections and air-flow during the flow-through portions of the cycle further reduced the necessary exposure time.

TABLE III

PRELIMINARY FLOW-THROUGH CYCLE FOR BRASS SPORE[a] INACTIVATION RESULTS WHEN CONNECTED TO THE CHAMBER EXHAUST

| Exposure Time, min. | Spore Survivors, CFU |
|---|---|
| 15 | 0, 0 |
| 10 | 10, 14 |
| 7 | 4, 20 |
| 6 | 154 |
| 5 | 300 |
| 4 | 105 (18 sample avg.) |
| 4[b] | 16 (27 sample avg.) |

[a]Initial spore population in lumens was >10$^6$
[b]Flow 10 sec on/10 sec off

Comparing the 4 minute exposure with alternating 10 second flow and hold times and the 4 minute flow-through exposure times, the data show that there were approximately 10 times fewer survivors when hold times were utilized. Both cycles employed a deep vacuum injection pulse prior to the flow-through phase.

Spore inactivation in lumens is more efficient if the flow-through is started and stopped during sterilant vapor exposure. This is partially due to the elimination of channeling effects and partially due to diffusion (in flow-through lumens) into nooks and crannies. It is also believed that the process of the present invention allows the sterilant molecules to penetrate crevices within the construction of the lumened instrument so that the sterilant can react with the bacterial spores present there and thus, reduces the necessary exposure time to achieve sterilization. Another advantage to the deep vacuum flow-through cycle of the present invention is a savings on liquid sterilant usage by as much as 50%, thus reducing per cycle operating costs to the sterilizer user.

A fiber optic dental handpiece obtained from the manufacturer was subjected to 4,165 cycles of the sterilization method of the present invention. The fiber optic handpiece was then returned to the manufacturer for evaluation. The manufacturer's evaluation determined that the performance of the handpiece after so many repeated sterilization cycles was equal to that of a new handpiece. Steam sterilization would have destroyed numerous handpieces in an equivalent number of cycles.

The success of the tests with the fiber optics handpiece prompted the testing of other synthetic materials in prototype units. Items such as false teeth, crowns, caps, and dental impressions were all processed using the method of the present invention without adverse affects.

Fiber optics and lumen processing capability make this process an ideal candidate for sterilization of endoscopes. Cassettes could be used to hold the endoscope in a manner similar to that proposed for dental handpieces during sterilization and afterwards, for storage capable of maintaining sterility.

The apparatus of FIG. 4 was submitted to the FDA and EPA and has been approved. In connection with the FDA submission, tests were performed to demonstrate microbial effectiveness using AOAC sporicidal testing procedures. To accomplish sterilization of the 720 carriers specified by the AOAC, the cycle of FIG. 1 included five deep vacuum injections alternated with four flow-through injections each lasting 100 seconds. In the cycle of FIG. 3, an additional deep vacuum injection plus another two flow-through injections were employed, but the flow-through portions of the cycle of FIG. 3 were each 70 seconds in length.

Table IV lists the results of the sporicidal testing for the cycle of FIG. 1 in the apparatus of FIG. 4. Table V lists the results of the sporicidal testing for the cycle of FIG. 3 in the apparatus of FIG. 4. At the same time the cycles of FIGS. 1 and 3 were able to sterilize inoculated product in at least half cycle contact times. In FIG. 1, for example, when n=4, half cycle contact time would be n=2. Also, the last deep vacuum injection at point F was eliminated, so the exposure time for these tests was 44% of the typical total sterilization time. In FIG. 3, for example, when n=6, half cycle time would be n=3 so that the exposure time for these tests was 50% of the typical total sterilization time. Tables VI through IX list the results of the test run at half cycle times.

TABLE IV

AOAC SPORICIDAL TEST RESULTS HIGHSPEED HANDPIECE/BUR CYCLE[1]

| TEST | | NUMBER POSITIVE/ NUMBER EXPOSED | |
|---|---|---|---|
| ORGANISM | CARRIER | 1st TRANSFER | 2nd TRANSFER |
| B. subtilis | PC[2] | 0/60 | 0/60 |
| ATCC 19659 | SL[3] | 0/60 | 0/60 |
|  | PC | 0/60 | 0/60 |
|  | SL | 0/60 | 0/60[4] |
|  | PC | 0/60 | 0/60 |
|  | SL | 0/60 | 0/60 |
| C. siporogenes | PC | 0/60 | 0/60 |
| ATCC 3584 | SL | 0/60 | 0/60 |
|  | PC | 0/60 | 0/60 |
|  | SL | 0/60 | 0/60 |

[1]Average exposure time of 13.6 minutes and cycle time of 16.3 minutes
[2]Penicylinder
[3]Suture loop
[4]Identified a gram (+) short rod; B. subtilis not recovered from the tube

TABLE V

AOAC SPORICIDAL TEST RESULTS INSTRUMENT CYCLE[1]

| TEST | | NUMBER POSITIVE/ NUMBER EXPOSED | |
|---|---|---|---|
| ORGANISM | CARRIER | 1st TRANSFER | 2nd TRANSFER |
| B. subtilis | PC[2] | 0/60 | 0/60 |
| ATCC 19659 | SL[3] | 0/60 | 0/60 |
|  | PC | 0/60 | 0/60 |
|  | SL | 0/60 | 0/60 |
|  | PC | 0/60 | 0/60 |
|  | SL | 0/60 | 0/60 |
| C. siporogenes | PC | 0/60 | 0/60 |
| ATCC 3584 | SL | 0/60 | 0/60 |
|  | PC | 0/60 | 0/60 |
|  | SL | 0/60 | 0/60 |

[1]Average exposure time of 15.8 minutes and cycle time of 21.5 minutes
[2]Penicylinder
[3]Suture loop The results demonstrate that both cycles were able to sterilize 720 carriers (180 of each of the four types) in twelve replicate cycles. One positive occurred in the second transfer of a B. subtilis penicylinder, sterilized during the cycle of FIG. 1; however, a gram stain indicated that the organism was a gram positive short rod and not the indicator organism.

TABLE VI

STERILIZATION OF INOCULATED PRODUCT SAMPLES DURING THE CYCLE OF FIG. 1 AT 44% OF THE ESTIMATED CONTACT TIME (100 SECOND FLOW-THROUGH INJECTIONS)

| Inoculated Product Samples | B. stearothermophilus sterility results |
|---|---|
| Handpiece Lumens (2 high speeds and sonic scaler) | 0/1[1] |
|  | 0/1 |
|  | 0/3 |
|  | 0/3 |
|  | 0/3 |
|  | 0/3, 0/3, 0/3 |
| Total Lumens | 0/20 |
| Internal Surfaces of Handpieces (2 High speeds and sonic scaler) | 0/3, 0/3, 0/3 |
| Total Internal Surfaces | 0/9 |
| Burs (carbide & diamond) | 0/4 |
|  | 0/4 |
|  | 0/4 |
|  | 0/4 |
|  | 0/4 |
|  | 0/4, 0/4, 0/4 |
| Total Burs | 0/32 |
| Stainless Steel Coupons | 0/10, 0/10, 0/10 |
| Total Coupons | 0/30 |

[1] The number of coupons testing positive for growth per the number tested

TABLE VII

Figure 2:
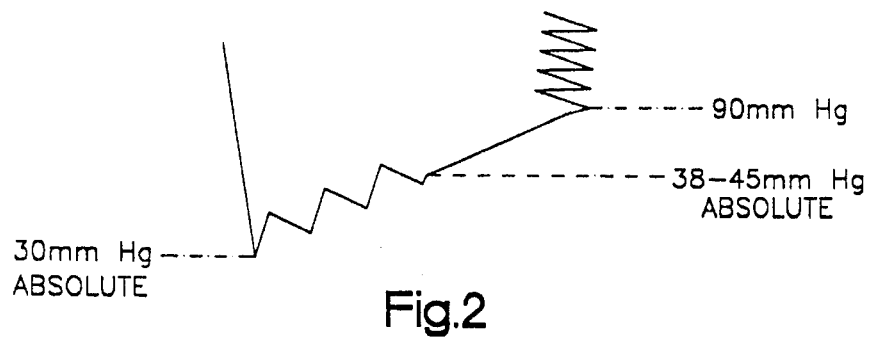
FIG. 2 is an enlarged portion in the graph of FIG. 1.

STERILIZATION OF INOCULATED PRODUCT SAMPLES DURING THE CYCLE OF FIG. 2 AT 50% OF THE ESTIMATED CONTACT TIME (70 SECOND FLOW-THROUGH INJECTIONS)

| Inoculated Product Samples | B. stearothermophilus sterility results |
|---|---|
| Handpiece Lumens (2 high speeds and 1 sonic scaler) | 0/3[1] |
|  | 0/1 |
|  | 0/3 |
| Total Lumens | 0/7 |
| Low Speed Handpiece Component | 0/7 |
|  | 0/7 |
|  | 2/7 |
| Total Low Speeds Prostheses/Dental Instruments | 2/21 |
|  | 0/8 |
|  | 1/8 |
|  | 2/8 |
| Total Prostheses/Instruments | 3/24 |
| Burs (carbide and diamond) | 0/4 |
|  | 0/4 |
|  | 0/4 |
| Total Burs | 0/12 |

[1] The number of coupons testing positive for growth per the number tested

TABLE VIII

STERILIZATION OF INOCULATED PRODUCT SAMPLES DURING THE CYCLE OF FIG. 2 AT 50% OF THE ESTIMATED CONTACT TIME (100 SECOND FLOW-THROUGH INJECTIONS)

| Inoculated Product Samples | B. stearothermophilus sterility results |
|---|---|
| Handpiece Lumens (2 high speeds and 1 sonic scaler) | 0/3[1] |
|  | 0/3 |
|  | 0/3 |
| Total Lumens | 0/9 |
| Internal Surfaces of Handpieces (2 highspeed and 1 sonic scaler) | 0/3 |
|  | 0/3 |
|  | 0/3 |
| Total Internal Surfaces | 0/9 |
| Low Speed Handpiece Components | 0/14 |
|  | 0/14 |
|  | 0/14 |
| Total Low Speeds Prostheses/Dental Instruments | 0/42 |
|  | 0/8 |
|  | 0/8 |
|  | 0/8 |
| Total Prostheses/Instruments | 0/24 |
| Burs (carbide and diamond) | 0/4 |
|  | 0/4 |
|  | 0/4 |
| Total Burs | 0/12 |
| Stainless Steel Coupons | 0/30 |
|  | 0/30 |
|  | 0/30 |
| Total Coupons | 0/90 |

[1] The number of coupons testing positive for growth per the number tested

TABLE IX

STERILIZATION OF INOCULATED STAINLESS STEEL COUPONS DURING THE CYCLE OF FIG. 2 AT 50% OF THE ESTIMATED CONTACT TIME (100 SECOND FLOW THROUGH INJECTIONS) UNDER VARIOUS AMBIENT CONDITIONS

| Temperature (°C.) | % Relative Humidity | B. stearothermophilus Sterility results |
|---|---|---|
| 38 | 88 | 0/30[1] |
| 38 | 89 | 0/30 |
| 38 | 91 | 0/30 |
| 19 | 55 | 0/30 |
| 18 | 60 | 0/30 |
| 18 | 52 | 0/30 |

The results of Table VI demonstrate that the estimated contact time for the cycle of FIG. 1 is adequate since replicate samples of inoculated product and of coupons distributed throughout the chamber were sterilized after a 2 phase cycle (n=2) of 44% of the estimated contact time.

The initial estimated contact time for the cycle of FIG. 2, as determined by the EPA/AOAC Sporicidal Test, was shown to be inadequate since partial positives were observed for some of the inoculated products at the half exposure time (Table VII). The irregular surfaces of the low speed handpiece components seemed to accumulate the spore suspension in one localized area, thereby, making a thicker inoculum. Samples of metallic bridge material were also more difficult to sterilize since their surfaces were porous. However, as shown in Table VIII, the addition of 30 seconds to each sterilant flow-through injection in the cycle of FIG. 2 permitted replicate samples of inoculated product and of coupons distributed throughout the chamber to be sterilized within 3 phases (n=3) or 50% of the estimated contact time.

Elevated ambient relative humidities, which a sterilizer may encounter, were shown by the results of Table IX to have no effect on sterilization efficacy.

What we claim is:

1. Apparatus for sterilizing items having at least two open ends and a fluid flow path between the open ends comprising:

a sterilization chamber having an inlet port and an exhaust port;

manifold means fluidly coupled to either the inlet port or the exhaust port and having a plurality of seats, each seat for fluid connection to fluid flow paths of one item;

means for creating a negative pressure differential downstream of the exhaust port;

a source of liquid sterilant;

means for vaporizing the liquid sterilant;

valve means intermediate the source of liquid sterilant and the vaporizing means for pulsing successive increments of liquid sterilant into the vaporizing means;

fluid connection means for fluidly connecting the source of liquid sterilant, the valve means, the vaporizing means and the chamber;

an air flow path through the vaporizing means and at least that portion of the fluid connection means passing from the vaporizing means to the chamber;

means for opening the exhaust port to flow the sterilant vapor and air through the inlet port and out of the chamber through the outlet port for a first period of time while maintaining the chamber pressure at a subatmospheric predetermined level, and for closing the exhaust port to stop the flow of sterilant vapor and air into and out of the chamber for a second period of time while maintaining the chamber pressure at said predetermined subatmospheric pressure; and means for successively repeating in an alternating fashion the flowing and the stopping of the flow of sterilant vapor and air into and out of the chamber a plurality of times while maintaining the chamber pressure at said predetermined subatmospheric pressure.

2. The apparatus recited in claim 1 further comprising means for converting the sterilant vapor into constituents thereof suitable for disposal, said converting means being fluidly connected to the exhaust port of the chamber downstream of the means for creating negative pressure.

3. The apparatus recited in claim 1 wherein said chamber is a freeze dryer.

4. The apparatus recited in claim 1 wherein the inlet and exhaust ports of the chamber are constructed for releasable fluid connection to at least one removable member, said removable member being constructed to hold said items during a sterilization process so that said items are sterilized within said removable member when subjected to the sterilization process.

5. The apparatus recited in claim 4 wherein the manifold means are positioned in the at least one removable member for fluidly connecting said items to either said inlet or said exhaust ports such that sterilant vapor will flow through the fluid flow paths of the items during the sterilization process.

6. The apparatus recited in claim 4 wherein the removable member comprises first and second extension ports and wherein the inlet port and the exhaust port of the chamber each define a channel for fluid connection to the first and second extension ports, said channel housing a receiving member for receiving one of the first or second extension ports, a blocking member and an actuation member operatively connecting the receiving and blocking member and structured for slidable axial movement through the length of the channel;

means for limiting the travel of said actuation member within the channel; and a bypass conduit fluidly joining the inlet channel and the exhaust channel, wherein when the first and second extension ports are inserted into the receiving members of each channel, each receiving member slides along a portion of each channel to effect the movement of each blocking member from a first position wherein the bypass conduit is open to a second position wherein the bypass conduit is closed.

* * * * *